United States Statutory Invention Registration [19]

[11] Reg. Number: H759

Jones [43] Published: Apr. 3, 1990

[54] E-Z CUSTOM ICE PACKS

[76] Inventor: Stanley J. Jones, Rte. 2, Box 735, Bush, La. 70431

[21] Appl. No.: 197,330

[22] Filed: May 23, 1988

[51] Int. Cl.[4] ..... A61F 7/00

[52] U.S. Cl. ..... 128/402; 128/403; 128/379

[58] Field of Search ..... 128/402, 403, 379; 62/530

[56] References Cited

U.S. PATENT DOCUMENTS

| | | | |
|---|---|---|---|
| 2,011,832 | 8/1935 | Slater | 62/530 |
| 2,203,591 | 6/1940 | Brown | 62/530 |
| 2,378,087 | 6/1945 | Kearney | 62/530 |
| 2,547,886 | 4/1951 | Poux | 128/402 |

FOREIGN PATENT DOCUMENTS

| | | | |
|---|---|---|---|
| 3411357 | 10/1985 | Fed. Rep. of Germany | 128/403 |
| 1185811 | 3/1970 | United Kingdom | 128/402 |

*Primary Examiner*—Charles T. Jordan

*Assistant Examiner*—Michael J. Carone

*Attorney, Agent, or Firm*—Lewis Arnold Thaxton

[57] ABSTRACT

This invention is directed to a flexible and resilient ice pack wrap used in cold therapy to relieve pain, swelling and edema to the user. The appliance comprises a rectangular or polyganol shaped polymer pack filled with a hydrophilic liquid coolant. The ice pack and contained coolant exhibits (a) flexibility, (b) pliability, and (c) complete contouring when applied to one's affected body surface.

3 Claims, 5 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

E-Z CUSTOM ICE PACKS

BACKGROUND OF THE INVENTION

This invention is directed to the field of instruments used as cold packs and their application to various areas of the human body. The inventive ice packs are specifically directed to a unique design, and because of that unique design, a more convenient and versatile application of the invention is now permitted.

In a good deal of post-operative surgery and injuries to the muscles, it remains both a need and conventional practice to apply ice packs for the relief of pain and swelling. Such a long-standing need and use of ice packs seems to have inspired health professionals and laity alike, to develope ice packs that can be applied from one's head to one's toes.

Resultingly, the art is replete with devices constructed to be filled with a cold solution and then positioned on an affected area of the human body. More recently, other ice packs contain a hydrophilic liquid as coolant that is first frozen and then the cold pack is applied to the user.

However, whether refillable with water or permanently filled with an organic liquid or gel, the prior art ice packs are generally bulky, heavy, cumbersome, uncomfortable, and frequently fail to remain properly positioned over the affected area of the wearer.

It is the overall object of this invention to set forth an ice pack that overcomes the aforementioned disadvantages of the prior art instruments and provides an improvement which renders a valued contribution to the advancement of the ice pack art.

It is consequently the primary object of the present invention to provide a new and improved ice pack device.

It is a further object of the present invention to provide an ice pack that is permanently filled with a hydrophilic coolant that can be refrozen after thawing.

It is an additional object of this invention to provide an ice pack having a plurality of small gel-filled compartments.

It is still another object of the present invention to provide an ice pack that is readily contoured to fit the user's foot, ankle, knee, leg, hand, wrist, arm, and other body areas.

Another object of this invention is to provide an ice pack possessing such a configuration that, when applied to a body area, particularly an extremity of the user, the ice pack remains in its correct position while the user is fully mobile.

It is yet another object of this invention to provide an ice pack which is equipped with fastening means commonly marketed under the trade name of VELCRO.

Other objects and advantages of this invention will become more fully apparent as this description proceeds, with reference being made to the accompanying drawings and appended claims.

SUMMARY OF THE INVENTION

Accordingly, the present invention has been developed with a set of views toward providing an advancement in the art of ice packs. The new and improved ice packs comprise a generally rectangular or polyganol shaped implement consisting of a unit cooling piece equipped with small elongated compartments containing a hydrophilic cooling material, i.e. propylene glycol.

The unit wrap consists of Velor rubber and Ace bandage material, both materials imparting a preferable measure of pliability to the ice packs. This preferred embodiment is directed to the foregoing material combination since such a combination is flexible and exhibits negligible, to no deformation of structure due to exposure to freezing temperatures, such as the freezing portion of a refrigerator. Since, at the time of manufacture, the coolant is hermetically sealed in individualized compartments, it is desirous to select a unit wrap type of material that permits a durable hinge of these plural compartments so that the unit wrap may effectively conform to the contour of various parts of the wearer's anatomy.

The ice packs of this invention are secured in place by the commonly used and commercially well-known VELCRO fasteners.

The invention, together with other features and advantages thereof, can be further enabled by reference to the following description taken in conjunction with the accompanying illustrative drawings.

DETAILED DESCRIPTION OF THE INVENTION

Figure 1:
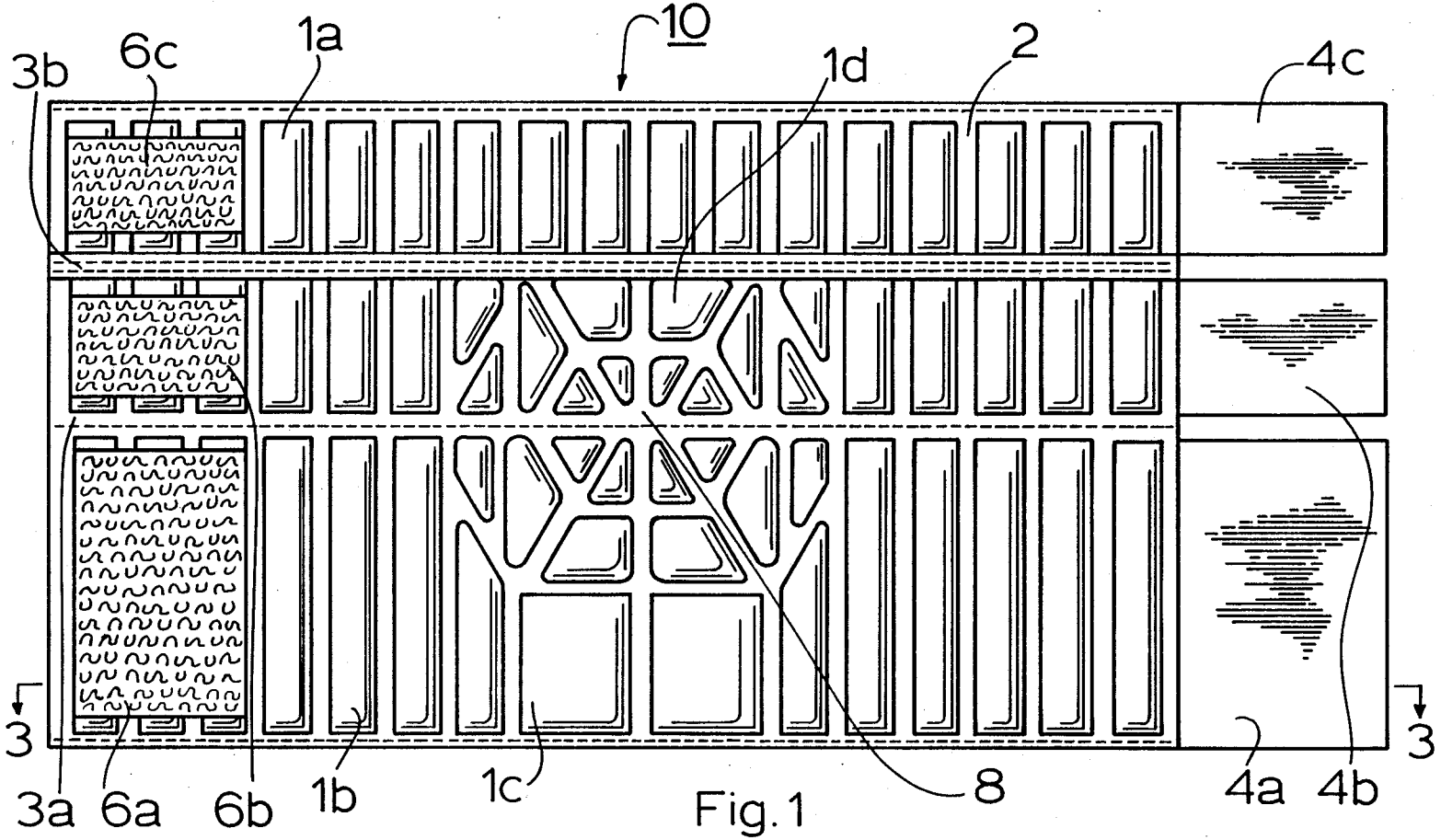
FIG. 1 is an outside plan view of one embodiment of the invention showing sundry configurations of the coolant compartments.
Figure 2:
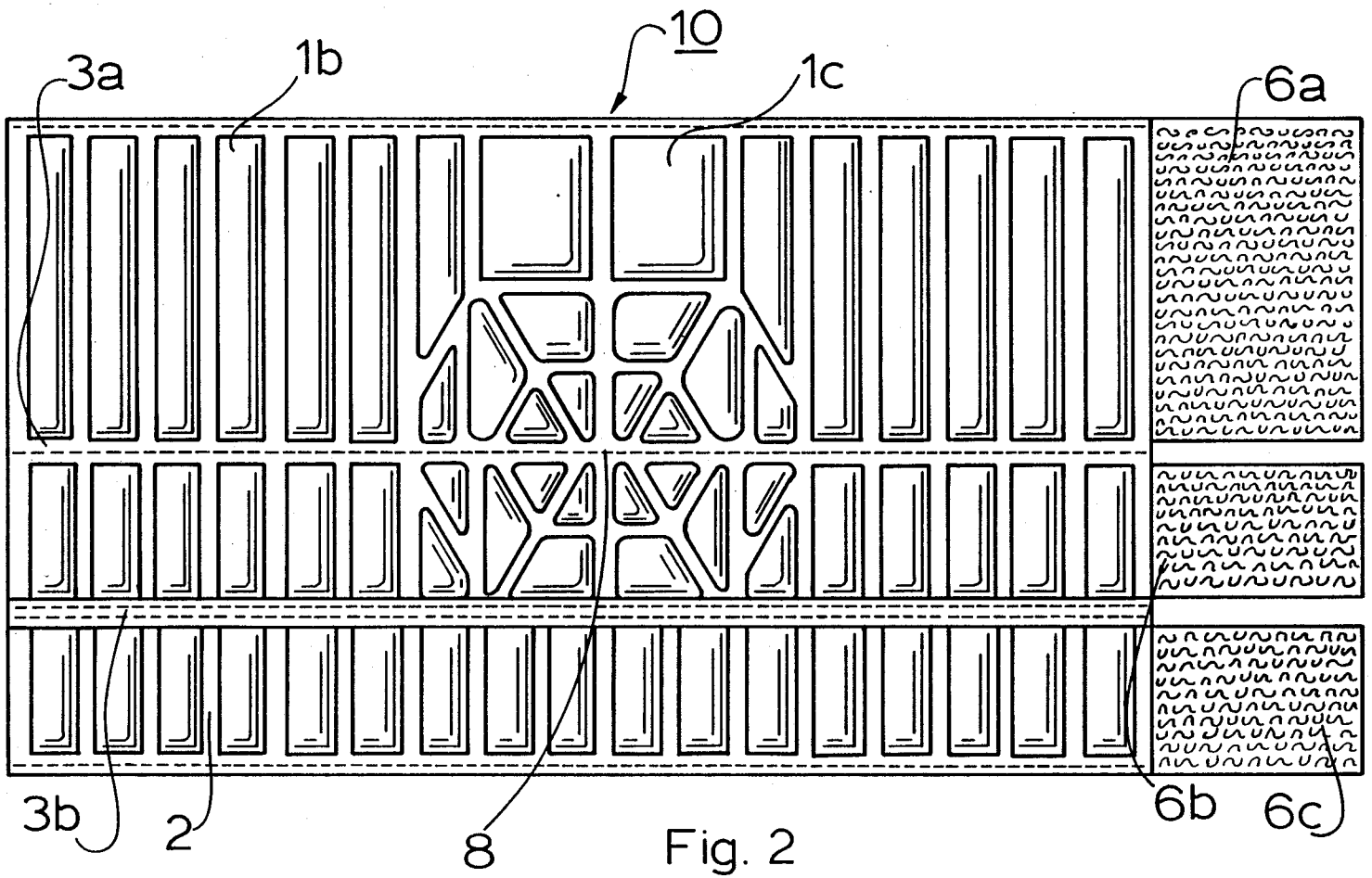
FIG. 2 is a rear plan view of FIG. 1.

Referring now to the drawings, wherein like numerals refer to like parts throughout the several views, and FIGS. 1 to 5 illustrate a simulative composite and preferred embodiment of the invention. FIGS. 1 and 2 illustrate the major construction of this invention, wherein the numeral 10 generally designates an ice pack embodying principles of the present invention. Small compartments 1*a* thru 1*h* are provided throughout and consists of a liquid impermeable substance, preferably Velor rubber, in which a hydrophilic coolant is contained. Multiple hinges 2, 3*a*, and 3*b* are variously adjacent to the liquid filled compartments 1*a* thru 1*h*, to facilitate and maintain flexibility of the ice pack 10. The ice pack 10 is further shown with adjustable attachment means comprising VELCRO strips 4*a*, 4*b*, 4*c*, 6*a*, 6*b*, and 6*c* cemented at the extremities of the pack.

Figure 3:
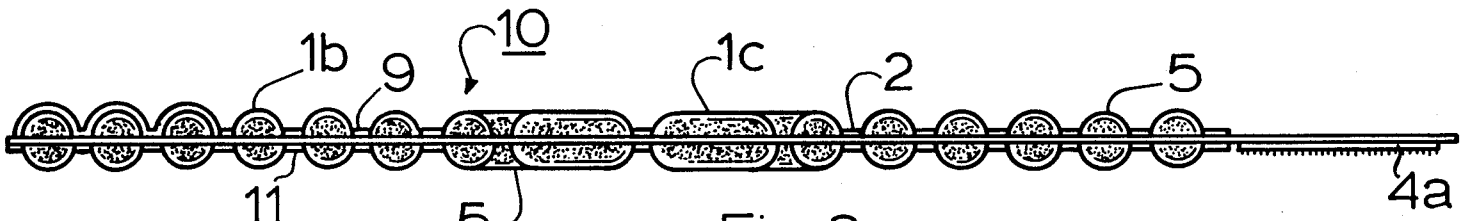
FIG. 3 is a bottomed cross-sectional view of FIG. 1 taken along line 3—3.

According to the invention, small compartments 1*a* thru 1*h* are first filled with a liquid 5, as best shown in cross-sectional view at FIG. 3. Liquid 5 is frozen within compartments 1*a* thru 1*h* when subjected to freezing temperatures. Each of compartments 1*a* thru 1*h* is first filled with the liquid 5 and then hermetically sealed. The small and varied shaped compartments 1*a* thru 1*h* are a significant embodiment of this invention, because it is owe to such configurations that versatility of application for ice pack 10 is imparted to the user. Ice pack 10 is readily and successfully applied, due to the design feature, to a relatively flat body surface. On the other hand, the artisan is able to appreciate that in those instances wherein the body surface area to be attended is rounded or curved, that improved and fully successful contact with that particular surface area is provided by means of ice pack 10.

The ice pack 10 of the invention further comprises a polygonal centered region 8 which exhibits enhanced flexibility to the user, particularly when the ice pack must fit over an elbow, knee or body member in addition to covering the surrounding surface area.

Figure 4:
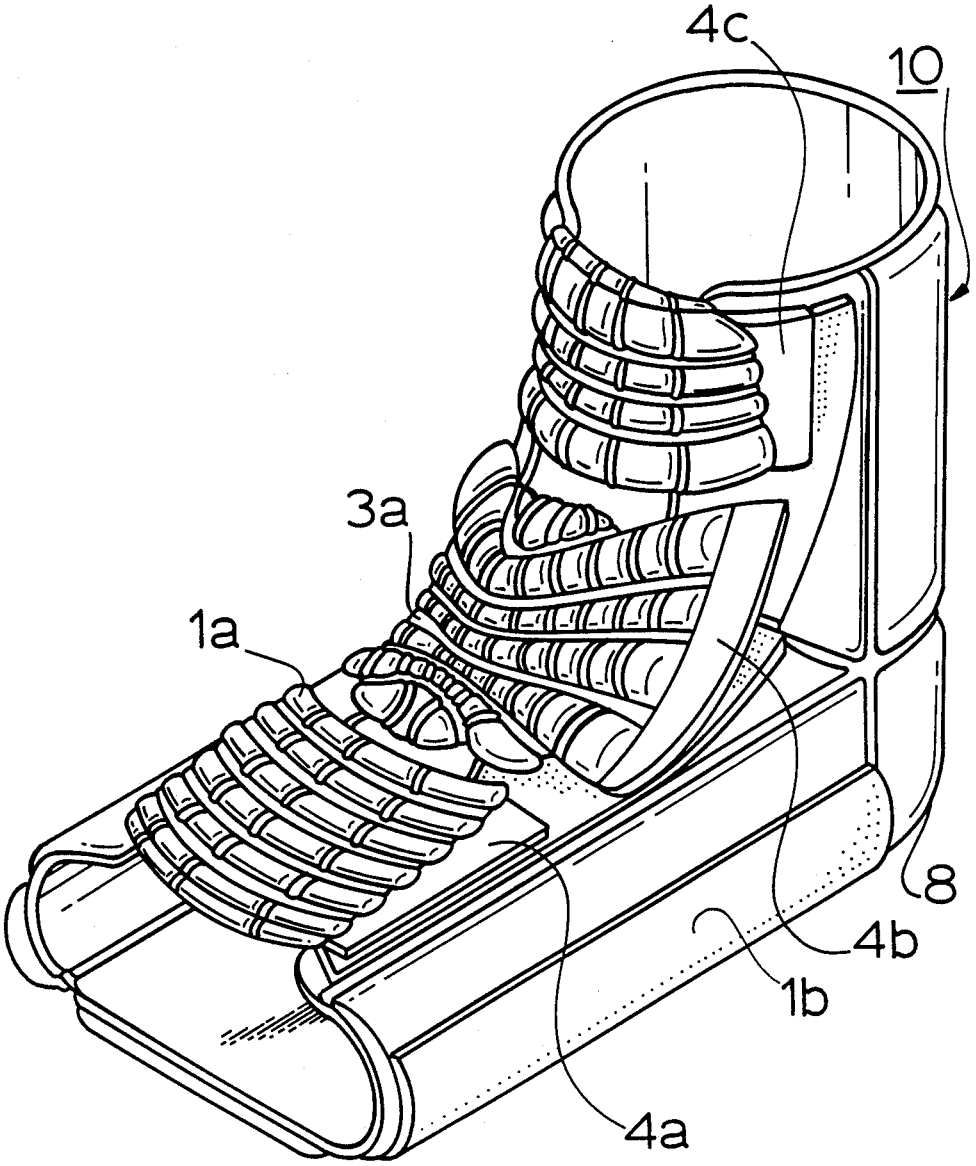
FIG. 4 is a perspective view of one embodiment of this invention showing the installation of an ice pack mounted on a wearer's foot.
Figure 5:
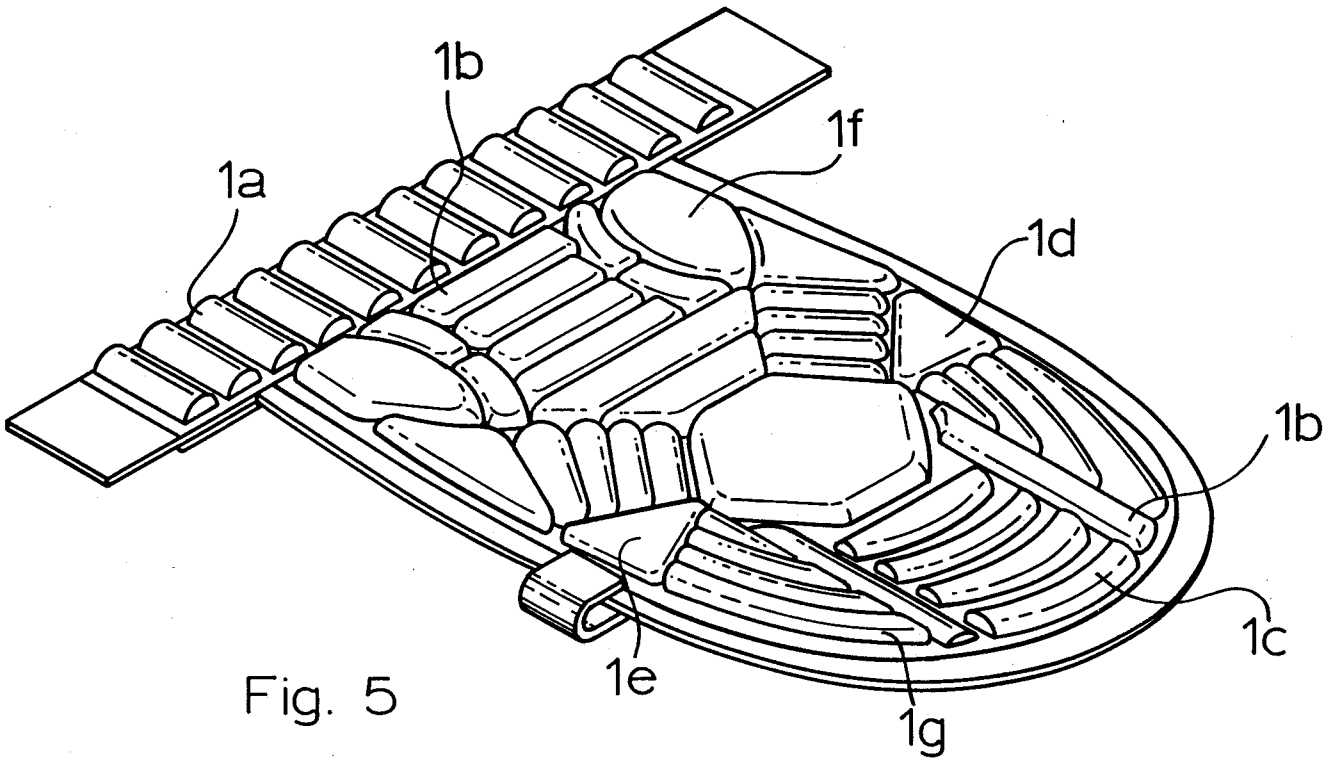
FIG. 5 is an isometric view of an ice pack, of this invention, which is of suitable use for the hand-wrist of the wearer.

FIGS. 4 and 5, respectively, are directed to another embodiment of the present invention, and shows the application of ice pack 10 comfortably secured about the foot and hand-wrist of the wearer.

Inexpensive manufacturing procedures using present day materials and technology can assemble ice pack 10 in its entirety. Preformed or sculptured Velor rubber sheet 11 is placed on a flat surface and each compartment 1*a* thru 1*h*, generally, is filled with a coolant 5. Matingly preformed sheet 9, which is also comprised of Velor rubber is then placed over sheet 11. Both sheets 9 and 11 are heat treated to attain a hermetic seal of all compartments therebetween. Lastly, the VELCRO strips are cemented to eachextremity and on the same side of ice pack 10.

It is to be understood that numerous modifications of the disclosed embodiments of the subject invention will undoubtedly occur to those of skill in the art and the spirit and scope of the invention is to be limited solely in light of the appended claims.

I claim:

1. An ice pack for cooling the affected body surface of a human being comprising:

a flexible rectangular or polyganol shaped wrap, said wrap consisting of two layers of rubber sheets heat sealed to contain small individualized compartments filled with propylene glycol coolant;

multiple hinge means between said compartments to provide flexibility and versatility to the user; and detachable fasteners for securing said ice pack comfortably around the user's applied body surface.

2. An ice pack in accordance to claim 1, wherein the wrap is rectangular in donfiguration.

3. An ice pack in accordance to claim 1, wherein the wrap is polyganol in configuration.

* * * * *